(12) United States Patent
Arnaud et al.

(10) Patent No.: US 6,649,173 B1
(45) Date of Patent: *Nov. 18, 2003

(54) TRANSFER-FREE TOPICAL COMPOSITION COMPRISING A FLUORINATED SILICONE COMPOUND AND ITS USE

(75) Inventors: Pascal Arnaud, L'Hay les Roses (FR); Sophie Beaumard, Chevilly Larue (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 115 days.

(21) Appl. No.: 08/978,974

(22) Filed: Nov. 26, 1997

(30) Foreign Application Priority Data

Nov. 26, 1996 (FR) ............................................. 96 14483
Nov. 26, 1996 (FR) ............................................. 96 14484

(51) Int. Cl.[7] ........................... A61K 7/42; A61K 7/021; A61K 7/025; A61K 7/06
(52) U.S. Cl. ........................... 424/401; 424/59; 424/63; 424/64; 424/70.7; 424/DIG. 5
(58) Field of Search .............................. 424/401, 63, 64, 424/59, 70.7, DIG. 5

(56) References Cited

U.S. PATENT DOCUMENTS 5,358,719 A * 10/1994 Mellul et al. ................ 424/497
5,589,165 A    12/1996 Yoshida et al. ........... 424/78.03
5,800,816 A *  9/1998 Brieva et al. .................. 424/63

OTHER PUBLICATIONS

English language abstract of JP2–295912, 1990.
English language abstract of JP9–295916, 1997.

* cited by examiner

*Primary Examiner*—Michael G. Hartley
*Assistant Examiner*—Marina Lamm
(74) *Attorney, Agent, or Firm*—Finnegan, Henderson, Farabow, Garrett & Dunner, LLP

(57) ABSTRACT

A topical composition, in particular a cosmetic composition, comprising, in a fatty phase, at least one wax and/or at least one nonvolatile liquid fatty substance, wherein the fatty phase contains at least one fluorosilicone compound. The composition exhibits good slip, non-tightness, softness and/or comfort properties as well as non-transfer and non-migration properties.

15 Claims, No Drawings

TRANSFER-FREE TOPICAL COMPOSITION COMPRISING A FLUORINATED SILICONE COMPOUND AND ITS USE

The subject of the present invention is a topical composition, in particular a cosmetic composition, which can be provided in the form of a stick or of a supple paste and which is capable of being used for caring for and/or making up the skin, semimucous membranes (such as the lips) and/or mucous membranes (such as the interior of the lower eyelids) of human beings and more especially the lips of the face.

Cosmetic or pharmaceutical compositions, such as lipsticks and foundations, generally comprise fatty substances, such as oils, pasty compounds and waxes, as well as a particulate phase generally composed of fillers and of pigments. They can also contain cosmetic or dermatological active principles (vitamins, screening agents, moisturizers). These compositions, when they are applied on the skin, the mucous membranes or the semimucous membranes, exhibit the disadvantage of transferring. This is understood to mean that the composition is capable of being deposited, at least in part, on certain substrates with which it is brought into contact, such as, for example, a glass, a cup, an item of clothing or the skin. On being deposited, the composition leaves a mark on the substrate. The result is thus a mediocre persistence of the composition on the skin or the mucous membranes, requiring it to be reapplied regularly. Moreover, the appearance of unacceptable marks on certain items of clothing and in particular on the collars of shirts or blouses might dissuade some consumers from using this type of makeup.

Another disadvantage of these compositions lies in the problem of migration. It has been found that certain cosmetic compositions have a tendency to spread into the fine lines and/or wrinkles of the skin, in the case of foundations; into the fine lines which surround the lips, in the case of lipsticks; and into the folds of the eyelid, in the case of eyeshadows. The appearance has also been found, in the case in particular of eyeshadows, of streaks in the makeup, due to the movements of the eyelids.

All these phenomena produce an unsightly effect which it is very clearly desirable to avoid.

For several years, many cosmetic scientists have been interested in "transfer-free" cosmetic compositions, in particular "transfer-free" lipstick or foundation compositions. Thus, Patent Application JP-A-61-65809 envisaged "transfer-free" lipstick compositions containing from 1 to 70% by weight of pulverulent silicone resin with silicate repeating units (or with a three-dimensional network) containing pendant alkylated or phenylated chains, the alkylated chains containing 1 to 6 carbon atoms, from 10 to 98% by weight of a cyclic volatile silicone oil and pulverulent fillers. However, these compositions exhibit the disadvantage of being liquid and thus rather inconvenient to use or at the very least far from the conventional concept of a lipstick in the form of a stick, thus limiting the number of consumers liable to use this type of lipstick. Moreover, the film obtained on the lips after evaporation of the silicone oil exhibits the disadvantage of becoming uncomfortable with time (feeling of desiccation and of tightness).

More recently, "transfer-free" lipsticks containing a cyclic or linear volatile silicone and a silicone resin containing a pendant esterified chain having at least 12 carbon atoms have been envisaged in Patent Application EP-A-602,905. The lipstick film exhibits in particular the disadvantage of lacking comfort on application, in particular of being too dry.

More recently still, the use has been envisaged, in these transfer-free compositions, of silicone resins modified by fluorinated groups (see the document EP-A 661,042). These resins, which are again provided in the pulverulent form, also result in compositions which are not very comfortable, desiccating and tightening the lips or the skin on which they are applied. Moreover, these resins are difficult to employ. Thus, it is preferable to mix them, prior to their use, with a volatile silicone oil, which involves an additional premixing stage, resulting in a significant additional cost during industrial production. Moreover, the necessary presence of a silicone oil in the introduction of the said resin results in an additional formulating constraint.

Generally, it is now known that, while the combination of volatile oils with certain compounds, in particular silicone compounds, makes it possible to obtain a satisfactory "transfer-free" result, it nevertheless exhibits the disadvantage of resulting, after evaporation of the volatile substances, in a film of non-optimum comfort, in particular because it is impossible to add oils other than silicone oils to these compositions while retaining a correct "transfer-free" quality. This is because hydrocarbon oils, which are known to contribute in particular comfort to a cosmetic or dermatological composition, have the disadvantage of increasing the transfer of such a composition.

Now, following in-depth studies, the inventors have demonstrated that, unexpectedly and surprisingly, it was possible to prepare a so-called "transfer-free" cosmetic composition which makes it possible, in particular, to obtain a film which does not transfer and which does not migrate and which exhibits improved cosmetic properties with respect to those of the "transfer-free" products of the prior art, in particular slip, non-tightness, softness and comfort properties.

This composition, with improved comfort with respect to the prior art, makes it possible to limit the transfer and/or the migration of the composition and thus makes it possible to improve the mechanical strength thereof, in particular toward rubbing and/or toward pressure.

A subject of the present invention is thus a topical composition comprising a fatty phase which contains at least one volatile compound, at least one wax and at least one nonvolatile liquid fatty substance, wherein the fatty phase contains at least one fluorosilicone compound of formula (I):

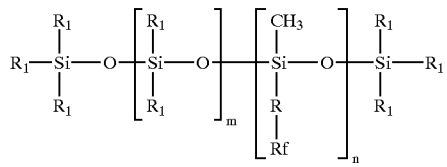

in which:

R represents, or independently represents, in the case when n is greater than 1, a linear or branched divalent alkylene group having from 1 to 6 carbon atoms, preferably a divalent methylene, ethylene, propylene or butylene group, Rf represents, or independently represents, in the case when n is greater than 1, a fluoroalkyl radical, in particular a perfluoroalkyl radical, having from 1 to 9 carbon atoms, preferably from 1 to 4 carbon atoms, $R_1$ represents, independently of one another, a $C_1$–$_{20}$ alkyl radical, a hydroxyl radical or a phenyl radical, m ranges from 0 to 150, preferably from 20 to 100, and n ranges from 1 to 300, preferably from 1 to 100, and the non-fluoro, nonvolatile liquid fatty substance(s) and/or non-fluoro wax(es) are selected so as to satisfy the following relationship:

$$0 \leq \Delta\delta \leq 5$$

in which:

$\Delta\delta[4\times(\delta D\text{ non-fluoro wax}-\delta D\text{ non-fluoro, nonvolatile liquid fatty substance})^2 + (\delta P\text{ non-fluoro wax}-\delta P\text{ non-fluoro, nonvolatile liquid fatty substance})^2 + (\delta H\text{ non-fluoro wax}-\delta H\text{ non-fluoro, nonvolatile liquid fatty substance})^2]^{1/2}$.

In this formula, $\delta D$ characterizes the London dispersion forces resulting from the formation of dipoles induced during molecular impacts; $\delta P$ characterizes the Debye interaction forces between permanent dipoles; and $\delta H$ characterizes the specific interaction forces (hydrogen bond, acid/base, donor/acceptor type and the like.

Another subject of the invention is the use, in a transfer-free topical composition, of a fatty phase as mentioned above, in order to obtain a composition exhibiting good slip, non-tightness, softness and/or comfort properties.

"Transfer-free" composition is understood to mean in particular, in the present description, a composition which does not transfer or transfers only to a very slight extent, that is to say which is not deposited on and/or does not stain and/or does not adhere to a substrate with which it is brought directly into contact. A composition of foundation or tinted cream type which does not stain a shirt or blouse (thus in particular resistant to rubbing due to the movement of the face and of the neck) as well as a composition of lipstick type which does not stain a substrate, such as a glass, a cup or the skin (thus resistant to the pressure due to the application of the lips on the said substrate) are in particular considered as "non-transfer" according to the present invention.

A further subject of the invention is a process for limiting, decreasing and/or preventing the transfer of a composition for making up or for caring for the skin, mucous membranes, semimucous membranes or superficial body growths which consists in introducing, into the composition, a fatty phase as defined above.

The composition of the present invention exhibits a mechanical strength, in particular toward rubbing and/or toward pressure, thus a resistance to rubbing, which is appropriate and is considered as very comfortable, on application and throughout the day.

The composition according to the invention especially finds a particularly advantageous application in the field of caring for and/or of making up the skin, mucous membranes, semimucous membranes and superficial body growths. Mucous membrane is understood to mean in particular the inner part of the lower eyelid, semimucous membranes includes, more particularly, the meaning of the lips of the face and superficial body growths is understood to mean the eyelashes, eyebrows, hair and nails.

Thus, the invention finds a very particular application in the field of products for making up the lips of the face but also products for caring for the lips, as well as in the field of products for making up and caring for the skin, such as foundations, concealers, self-tanning agents or antisun products.

A further subject of the invention is consequently a transfer-free composition for making up or for caring for the lips containing a fatty phase as defined above.

The composition according to the invention thus comprises at least one fluorosilicone compound, which can be a volatile compound, a nonvolatile liquid fatty substance, a wax or a mixture of these compounds. In a preferred embodiment, the fluorosilicone compound is provided in the form of a nonvolatile liquid fatty substance.

The specific combination of the fluorosilicone compound with specific oils and/or waxes, the entire mixture being combined with a volatile compound, makes it possible to obtain notable "transfer-free" properties while resulting in a film which is very highly comfortable on the substrate on which it is applied.

During the preparation of a composition according to the invention, a homogeneous mixture is obtained in which the fluorosilicone compound is completely dissolved or dispersed. When the composition is applied on a substrate, for example on the lips, the volatile compounds rapidly evaporate. Without being bound by the present explanation, it is possible to envisage that, in the composition remaining on the lips, the fluorosilicone compound will have a tendency to migrate toward the most distant part of said substrate, in other words will have a tendency to "climb" to the surface of the deposited film, which will have the consequence of leaving, in the part which is closest to the substrate and thus in direct contact with said substrate, principally the other fatty compounds and in particular the hydrocarbon oils which contribute comfort.

The fluorosilicone compound can preferably be represented by the following formula (II):

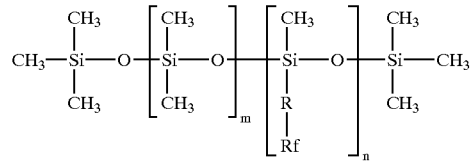

in which:

R represents, or independently represents, in the case when n is greater than 1, a linear or branched divalent alkylene group having from 1 to 6 carbon atoms, preferably a divalent methylene, ethylene, propylene or butylene group, Rf represents, or independently represents, in the case when n is greater than 1, a fluoroalkyl radical, in particular a perfluoroalkyl radical, having from 1 to 9 carbon atoms, preferably from 1 to 4 carbon atoms, m ranges from 0 to 150, preferably from 20 to 100, and n ranges from 1 to 300, preferably from 1 to 100.

In an even more preferred embodiment, the fluorosilicone compound used according to the invention has the following formula (III):

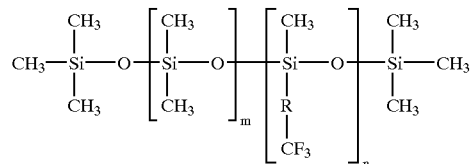

with

R representing, or independently representing, in the case when n is greater than 1, a divalent methylene, ethylene, propylene or butylene group, m ranging from 0 to 80, and n ranging from 1 to 30.

Such compounds are in particular those sold by Shin Etsu under the names "X22-819", "X22-820", "X22-821" and "X22-822" or alternatively "FL-100".

It is very clearly possible to use a mixture of several fluorosilicone compounds. The nonvolatile liquid fatty substances can in particular replace all or part of the liquid fatty substances of the composition.

Moreover, the composition according to the invention can comprise any compound known to a person skilled in the art for the type of application envisaged which does not destroy the desired properties.

In a preferred embodiment, the composition is anhydrous.

The fluorosilicone compound can preferably be present in the composition in the proportion of 0.1 to 40% by weight, preferably 3 to 30% by weight, with respect to the total weight of the composition.

The composition according to the invention preferably comprises at least one compound which is volatile at room temperature (20–25° C.), which can thus be fluorinated or non-fluorinated. Volatile compound is understood to mean, in the present description, any compound capable of evaporating on contact with the skin. Use is preferably made of volatile oils with a flashpoint sufficiently high to enable these oils to be used in formulation and sufficiently low for the desired evanescent effect to be obtained. Volatile oils are preferably employed with a flashpoint of the order of 40–100° C.

These volatile compounds can in particular be selected, alone or as a mixture, from hydrocarbon oils and/or silicone oils, which are cyclic or linear.

Mention may be made, alone or as a mixture, among volatile silicone oils, of volatile cyclic silicones having from 3 to 8 silicon atoms and preferably from 4 to 6. Examples are cyclotetradimethylsiloxane, cyclopentadimethylsiloxane and cyclohexadimethylsiloxane, cyclocopolymers of the dimethylsiloxane/methylalkylsiloxane type, such as Silicone FZ 3109, sold by the company called Union Carbide, which is a dimethylsiloxane/methyloctylsiloxane cyclocopolymer, volatile linear silicones having from 2 to 9 silicon atoms. Examples are hexamethyldisiloxane and a PDMS of low viscosity (1 cSt). Mention may alternatively be made of alkyltrisiloxanes, such as hexylheptamethyltrisiloxane or octylheptamethyltrisiloxane.

Mention may be made, among volatile hydrocarbon oils, of $C_8$–$C_{15}$ isoparaffins and in particular isododecane.

The composition according to the invention can preferably comprise 8 to 99% by weight, more preferably 15 to 85% by weight and most preferably 30 to 70% by weight of volatile compounds with respect to the total weight of the composition.

The composition also comprises at least one wax which can be fluorinated or non-fluorinated or a mixture of different waxes, so as to help in conferring, in particular, mechanical strength on the composition, when it is provided in the form of a stick. When it is provided in the form of a supple paste or a cast product, the composition according to the invention can comprise a lower amount of wax.

Any wax known in the prior art can be employed, among which, alone or as a mixture, may be mentioned waxes of animal, vegetable, mineral and synthetic origin, such as microcrystalline waxes, paraffin, petrolatum, petroleum jelly, ozokerite, montan wax, beeswax, lanolin and its derivatives, candelilla, ouricury, carnauba and Japan waxes, cocoa butter, sugarcane or cork fiber waxes, hydrogenated oils which are solid at 25° C., ozokerites, fatty esters and glycerides which are solid at 25° C., polyethylene waxes and waxes obtained by the Fischer-Tropsch synthesis, silicone waxes and in particular alkylsilicone waxes, as well as fluorinated waxes, and their mixtures.

The waxes taking part in the composition can preferably exhibit a melting point greater than approximately 45° C. and in particular greater than 55° C., and/or a needle penetration index at 25° C. preferably of from 3 to 40.

The composition preferably comprises 0.5 to 30% by weight of wax, in particular 5 to 20% by weight, with respect to the total weight of the composition.

Moreover, the composition comprises at least one nonvolatile liquid fatty substance, which can be fluorinated or non-fluorinated. Liquid fatty substance is understood to mean a compound having a melting point of less than approximately 30–35° C., in contrast to solid fatty substances, such as waxes, which have a melting point greater than approximately 50° C.

Mention may be made, among liquid fatty substances which can be envisaged, of any nonvolatile liquid fatty substance known to a person skilled in the art for the application envisaged. Mention may particularly be made of oils of vegetable, mineral, animal, synthetic and/or silicone origin, and their mixtures.

Mention may be made, among silicone oils, of phenylated silicone oils, in particular of polyphenylmethylsiloxane or phenyltrimethicone type, and in particular of the oils corresponding to the following formula:

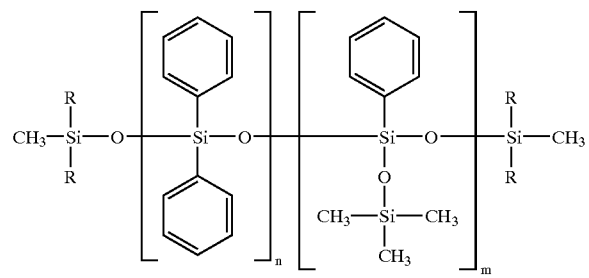

in which

R is independently a saturated or unsaturated, linear or branched $C_1$–$C_{30}$ alkyl radical, an aryl radical or an aralkyl radical, in $C_7$ and $C_{60}$, n is an integer ranging from 0 to 100, m is an integer ranging from 0 to 100, with the proviso that the sum m+n is selected from 1 to 100.

Mention may alternatively be made of poly($C_1$–$C_{20}$) alkylsiloxanes in which the alkyl group is saturated or unsaturated and linear or branched, and in particular those with terminal trimethylsilyl groups, among which mention may be made of linear polydimethylsiloxanes and of alkylmethylpolysiloxanes, alkyldimethicones or silicones modified by aliphatic and/or aromatic groups or by functional groups, such as hydroxyl, thiol and/or amine groups.

Mention may be made, among hydrocarbon oils of animal, vegetable, mineral or synthetic origin, of the oils formed by esters of fatty acids and of polyols, in particular liquid triglycerides, for example sunflower oil, maize oil, soybean oil, cucumber oil, liquid paraffin, liquid petrolatum, perhydrosqualene, groundnut oil, sweet almond oil, macadamia oil, grape seed oil, rapeseed oil, coconut oil, calophyllum oil, palm oil, castor oil, avocado oil, apricot oil, sesame oil, jojoba oil, olive oil or cereal germ oils, fish oils, glyceryl tricaprate/caprylate, fatty acid esters, alcohols, acetylglycerides, octanoates, decanoates or ricinoleates of alcohols or of polyalcohols, fatty acid triglycerides, glycerides, oils of formula $R_1COOR_2$, in which $R_1$ represents the residue of a higher fatty acid containing from 7 to 19 carbon atoms and $R_2$ represents a branched hydrocarbon chain containing from 3 to 20 carbon atoms, for example purcellin oil or wheat germ oil, and their mixtures.

In a preferred embodiment, the oils present in the composition are mainly hydrocarbons.

The composition according to the invention can preferably comprise 1 to 50% by weight of nonvolatile liquid fatty substance, in particular from 1 to 40% and better still from 5 to 30%, by weight.

Mention may be made, among other fatty substances capable of being present in the composition, of silicone gums and pasty fatty substances of vegetable, mineral, animal, synthetic and/or silicone origin. These fatty substances can in particular be chosen in a way varied by persons skilled in the art in order to prepare a composition having the desired properties, for example of consistency or of texture. These fatty substances can be both hydrocarbons and silicones, which makes it possible to adapt the properties of the film, in particular as regards the comfort on the lips or the skin of human beings.

The non-fluorinated, nonvolatile, liquid fatty substance(s) and/or the non-fluorinated wax(es) are selected so as to verify the following relationship:

$$\leq \Delta\delta \leq 5$$

and preferably $$\Delta\delta \leq 4$$

The distance $\Delta\delta$ represents the distance in Hansen space between the point representing the wax or the mixture of waxes and the point representing the nonvolatile liquid fatty substance or the mixture of nonvolatile liquid fatty substances.

The volatile compounds, the fluorinated nonvolatile liquid fatty substances and the fluorinated waxes are not taken into consideration during the calculation of the distance $\Delta\delta$.

The distance $\Delta\delta$ can be calculated in the following way:

$$\Delta\delta=[4\times(\delta D \text{ wax}-\delta D \text{ nonvolatile liquid fatty substance})^2+(\delta P \text{ wax}-\delta P \text{ nonvolatile liquid fatty substance})^2+(\delta H \text{ wax}-\delta H \text{ nonvolatile liquid fatty substance})^2]^{1/2}.$$

The definition of fatty substances in the three-dimensional solubility space according to Hansen is described in the article by C. M. Hansen: "The Three-dimensional Solubility Parameters", J. Paint Technol., 39, 105 (1967), the disclosure of which is specifically incorporated by reference herein.

According to the space described by Hansen:

$\delta D$ characterizes the London dispersion forces resulting from the formation of dipoles induced during molecular impacts;

$\delta P$ characterizes the Debye interaction forces between permanent dipoles;

$\delta H$ characterizes the specific interaction forces (hydrogen bond, acid/base, donor/acceptor type and the like);

The parameters $\delta P$, $\delta H$ and $\delta D$ are generally expressed in $(J/cm^3)^{1/2}$.

In the composition according to the invention, any fatty substance or mixture of fatty substances satisfying the above relationships can be used. In this case, the solubility parameters of the mixture are determined from those of the fatty substances taken separately, according to the following relationships:

$$\delta_{Dmix} = \sum_i xi\delta_{Di}; \quad \delta_{Pmix} = \sum_i xi\delta_{Pi} \quad \text{and} \quad \delta_{Hmix} = \sum_i xi\delta_{Hi}$$

where xi represents the fraction, by volume, of the fatty substance i in the mixture. It is within the capability of a person skilled in the art to determine the amounts of each fatty substance in order to obtain a mixture of fatty substances which satisfies the above relationships.

The composition can also comprise a particulate phase, which can comprise pigments and/or pearlescent agents and/or fillers commonly used in cosmetic and dermatological compositions. Pigments should be understood as comprising white or colored, inorganic or organic particles intended to color and/or opacify the composition. Fillers should be understood as comprising colorless or white, inorganic or synthetic, lamellar or non-lamellar particles intended to give body or stiffness to the composition, and/or softness, matteness and uniformity to the makeup. Pearlescent agents should be understood as comprising iridescent particles which reflect light.

The pigments can be present in the composition in the proportion of 0 to 15% by weight of the final composition and preferably in the proportion of 3 to 12% by weight. They can be white or colored, inorganic and/or organic, and of conventional or nanometric size. Mention should be made of titanium, zirconium or cerium dioxides, as well as of zinc, iron or chromium oxides, ferric blue, carbon black, ultramarines (aluminosilicate polysulfides), manganese pyrophosphate and certain metal powders, such as those of silver or of aluminum. Mention may alternatively be made of the lakes commonly employed to confer a makeup effect on the lips and on the skin, which are calcium, barium, aluminum or zirconium salts, acid dyes, such as hydrohalide dyes, azo dyes, anthraquinone dyes, and the like.

The pearlescent agents can be present in the composition in the proportion of 0 to 20% by weight, preferably at a level of the order of 1 to 10% by weight.

Mention may be made, among the pearlescent agents which can be envisaged, of natural mother-of-pearl, mica covered with titanium oxide, with iron oxide, with natural pigment or with bismuth oxychloride, and colored titanium oxide-coated mica.

The fillers, which can be present in a proportion of 0 to 30% by weight, preferably 1 to 15%, in the composition, can be inorganic or synthetic, lamellar or non-lamellar. Mention may be made of talc, mica, silica, kaolin, nylon or polyethylene powders, TEFLON, starch, boron nitride, microspheres, such as EXPANCEL (Nobel Industrie), POLYTRAP (Dow Corning) and silicone resin microbeads (TOSPEARLS from Toshiba, for example).

The composition can additionally comprise any additive conventionally used in the cosmetics or dermatological field, such as antioxidants, fragrances, essential oils, preservatives, thickeners, cosmetic active principles, moisturizers, vitamins, dyes, essential fatty acids, sphingolipids, self-tanning agents, such as DHA, or sunscreens.

The composition according to the invention can also comprise at least one active agent, among which may be mentioned agents which are active against microorganisms, in particular with an antiviral, antibacterial or antifungal activity, agents with an antiinflammatory or immunomodulatory activity, agents which antagonize neuromediators or which modulate the release of neuromediators, agents which modulate cell differentiation and/or cell proliferation and/or pigmentation and/or which regulate keratinization, agents which are active in the treatment and/or the prevention of cheilites, antihistamines or cicatrizing agents.

Of course, a person skilled in the art will take care to choose the possible additional compounds and/or their amount so that the advantageous properties of the composition according to the invention are not, or not substantially, detrimentally affected by the envisaged addition.

The composition according to the invention can be provided in the form of a stick, in the form of an oily liquid, optionally gelled or alternatively in the form of a supple paste with a viscosity which can be measured, said dynamic viscosity at 25° C. generally being from 1 to 40 Pa·s, measured with a Contraves TV rotary viscometer equipped with an "MS-r4" rotor at a frequency of 60 Hz, and better still ranging from 3 to 35 Pa·s.

The compositions according to the invention find an application in particular in the field of making up the skin, semimucous membranes, mucous membranes and/or superficial body growths and are then provided, for example, in the form of a lipstick, of a foundation, of a blusher, of an eyeshadow, of a mascara, of an eyeliner or of a concealer.

They can also be provided in the non-colored form, optionally containing cosmetic or dermatological active principles. They can then in particular be used as a care base for the lips or as a fixing base for a lipstick film, in order to limit the transfer and the migration of a care or makeup film and thus to increase its strength.

The compositions according to the invention can also be provided in the form of a product for caring for the skin, mucous membranes, semimucous membranes and/or superficial body growths, such as a gel, a cream, a balm or a lotion, of a hygiene or pharmaceutical product or alternatively of an antisun or self-tanning product.

The invention is illustrated by, but is in no way limited to, the following examples.

EXAMPLE 1

A lipstick stick is prepared which has the following composition

| | |
|---|---|
| fluorinated silicone (X22819 from Shin Etsu) | 8 g |
| polyethylene wax | 16 g |
| hydrogenated polyisobutene | 12 g |
| arachidyl propionate | 9.5 g |
| pigments | 9.5 g |
| cyclotetrapolysiloxane    q.s. for | 100 g |

The composition was prepared in the usual way, by heating the wax, the polyisobutene and the arachidyl propionate to 95° C. and by mixing them. The fluorinated silicone and the pigments were then added, followed, at 60° C., by the cyclotetrapolysiloxane (volatile silicone oil). The entire contents were mixed using a Moritz turbine mixer at a speed of 3000 rev/min. The homogeneous mixture obtained could then be poured at 85° C. into appropriate molds.

After cooling, a lipstick stick with a pleasant texture was obtained which applied uniformly on the lips and the film of which was very comfortable, while leaving no marks on external substrates after evaporation of the volatile oil (a few minutes). This is all the more noteworthy as the composition comprised a significant amount of hydrocarbon oil, which is not very favorable to the "transfer-free" effect.

This composition was applied on the left-hand side of the lips of several people. For comparison, a "transfer-free" lipstick of the prior art (COLOUR ENDURE from L'Oréal) was applied on the right-hand side of said lips. The lipsticks were allowed to dry at room temperature for 10 minutes and then the entire lips are applied to a sheet of paper.

A very faint, scarcely perceptible, trace of lipstick was observed on all the sheets of paper, both for the composition of the invention and for the composition of the prior art.

The $\Delta\delta$ value (polyethylene wax and hydrogenated polyisobutene) was 1.62.

EXAMPLE 2

A lipstick stick was prepared, as in Example 1, having the following composition:

| | |
|---|---|
| fluorinated silicone (X22820 from Shin Etsu) | 8 g |
| polyethylene wax | 16 g |
| squalene | 12 g |
| arachidyl propionate | 9.5 g |
| pigments | 9.5 g |
| cyclotetrapolysiloxane    q.s. for | 100 g |

A lipstick stick was obtained which made it possible to obtain a comfortable film and which simultaneously exhibited notable "transfer-free" properties.

The $\Delta\delta$ value (polyethylene wax and squalene) was 1.17.

EXAMPLE 3

A lipstick stick was prepared according to Example 1, having the following composition

| | |
|---|---|
| fluorinated silicone (X22819 from Shin Etsu) | 16 g |
| polyethylene wax | 16 g |
| hydrogenated polyisobutene | 4 g |
| arachidyl propionate | 9.5 g |
| pigments | 9.5 g |
| cyclotetrapolysiloxane    q.s. for | 100 g |

The $\Delta\delta$ value (polyethylene wax and hydrogenated polyisobutene) was 1.62.

A lipstick stick was obtained which made it possible to obtain a comfortable film and which simultaneously exhibited notable "transfer-free" properties.

EXAMPLE 4

A soft paste having the following composition was prepared

| | |
|---|---|
| fluorinated silicone (X22819 from Shin Etsu) | 20 g |
| polyethylene wax | 5 g |
| pigments | 10 g |
| cyclotetrapolysiloxane | qs 100 g |

The composition was prepared by heating the wax and the fluorinated silicone to 80° C. and mixing them together. The pigments were added and, at 60° C., the volatile silicone oil. The whole was mixed using a Moritz turbine mixer at a speed of 3000 rev/min. The homogeneous mixture obtained could then be poured, at 85° C., into suitable molds.

A soft paste which may be applied to the lips, which had a very creamy texture and which had good transfer-free properties was obtained, this paste allowing a very comfortable film to be obtained.

We claim:
1. A topical composition comprising a fatty phase, said fatty phase containing at least one volatile compound, at least one wax and at least one nonvolatile liquid fatty substance,
  wherein said fatty phase contains at least one fluorosilicone compound of formula (III):

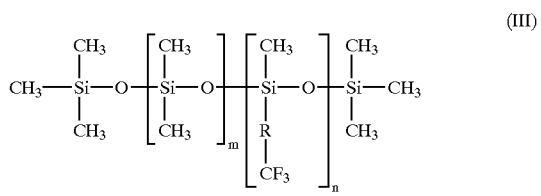

in which:
  R represents, or independently represents, in the case when n is greater than 1, a divalent methylene, ethylene, propylene or butylene group,
  m ranges from 0 to 80, and
  n ranges from 1 to 30,
  and wherein said at least one nonvolatile liquid fatty substance and said at least one wax are non-fluorinated compounds, and both said at least one nonvolatile liquid fatty substance and said at least one wax are selected so as to satisfy the following relationship:

$$0 \leq \Delta\delta \leq 4$$

in which:

$$\Delta\delta = [4 \times (\delta D \text{ non-fluoro wax} - \delta D \text{ non-fluoro, nonvolatile liquid fatty substance})^2 + (\delta P \text{ non-fluoro wax} - \delta P \text{ non-fluoro, nonvolatile liquid fatty substance})^2 + (\delta H \text{ non-fluoro wax} - \delta H \text{ non-fluoro, nonvolatile liquid fatty substance})^2]^{1/2}$$

wherein
  $\delta D$ characterizes London dispersion forces arising from formation of dipoles induced during molecular impacts;
  $\delta P$ characterizes the Debye forces of interaction between permanent dipoles; and
  $\delta H$ characterizes forces of specific interactions, and further wherein said at least one nonvolatile liquid fatty substance, said at least one wax, or both said at least one nonvolatile liquid fatty substance and said at least one wax, which are selected to satisfy the relationship $0 \leq \Delta\delta \leq 4$, are selected so as to impart to the composition simultaneously good properties of non-transfer and comfort.

2. A topical composition according to claim 1, wherein said fluorosilicone compound is present in the composition in an amount ranging from 0.1 to 40% by weight, relative to the total weight of the composition.

3. A topical composition according to claim 2, wherein said fluorosilicone compound is present in the composition in the amount of 3 to 30% by weight, relative to the total weight of the composition.

4. A topical composition according to claim 1, wherein said at least one volatile compound is selected from hydrocarbon oils and silicone oils, which oils are cyclic or linear.

5. A topical composition according to claim 1, wherein said at least one wax is a microcrystalline wax, paraffin, petrolatum, petroleum jelly, ozokerite, montan wax, beeswax, lanolin or a derivative, candelilla wax, ouricury wax, carnauba wax, Japan wax, cocoa butter, sugarcane wax, cork fiber wax, hydrogenated oil which is solid at 25° C., ozokerite, a fatty ester or a glyceride which is solid at 25° C., polyethylene wax, wax obtained by Fischer-Tropsch synthesis, or silicone wax.

6. A topical composition according to claim 1, wherein said at least one nonvolatile liquid fatty substance is an oil selected from nonvolatile hydrocarbon oils and nonvolatile phenylated silicone oils.

7. A topical composition according to claim 6, wherein said oil is selected mainly from nonvolatile hydrocarbon oils.

8. A topical composition according to claim 1, wherein said composition additionally comprises a particulate phase.

9. A topical composition according to claim 8, wherein said particulate phase comprises at least one of a pigment, pearlescent agent, or filler, or a mixture thereof.

10. A topical composition according to claim 1, wherein said composition is in anhydrous form.

11. A topical composition according to claim 1, wherein said composition is in the form of a stick, an oily liquid, or a supple paste with a dynamic viscosity at 25° C. ranging from 1 to 40 Pa·s.

12. A topical composition according to claim 1, wherein saide composition is in the form of a product for caring for, making up, or both caring for and making up the skin, lips of the face, superficial body growths, or any combination thereof.

13. A topical composition according to claim 1, wherein said composition is in the form of a lipstick, a foundation, a blusher, an eyeshadow, a mascara, an eyeliner, a care base for the lips, a fixing base, a care product, a hygiene or pharmaceutical product, an antisun product, or a self-tanning product.

14. A topical composition according to claim 12, wherein said composition exhibits at least one property selected from good slip, non-tightness, softness, and comfort, or any combination thereof, when used to care for, make up, or both care for and make up the skin, lips of the face, superficial body growths, or any combination thereof.

15. A process for limiting, decreasing, or preventing the transfer of a composition for making up, caring for, or both making up and caring for the skin, lips of the face, superficial body growths, or any combination thereof, said process comprising:
  introducing into said composition a fatty phase comprising at least one volatile compound, at least one wax, and at least one nonvolatile liquid fatty substance, wherein said fatty phase contains at least one fluorosilicone compound of formula (III):

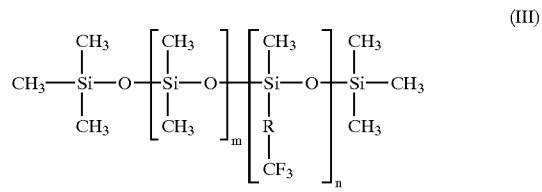

in which:
  R represents, or independently represents, in the case when n is greater than 1, a divalent methylene, ethylene, propylene or butylene group,
  m ranges from 0 to 80, and
  n ranges from 1 to 30, and wherein when at least one of said at least one nonvolatile liquid fatty substance and said at least one wax are non-fluorinated compounds, said at least one nonvolatile liquid fatty substance, said at least one wax, or both said nonvolatile liquid fatty substance and said wax are selected so as to satisfy the following relationship:

$$0 \leq \Delta\delta \leq 4$$

in which:

$$\Delta\delta = [4 \times (\delta D \text{ non-fluoro wax} - \delta D \text{ non-fluoro, nonvolatile liquid fatty substance})^2 + (\delta P \text{ non-fluoro wax} - \delta P \text{ nonfluoro, nonvolatile liquid fatty substance})^2 + (\delta H \text{ non-fluoro wax} - \delta H \text{ non-fluoro, nonvolatile liquid fatty substance})^2]^{1/2}$$

wherein $\delta D$ characterizes London dispersion forces arising from formation of dipoles induced during molecular impacts;

$\delta P$ characterizes the Debye forces of interaction between permanent dipoles; and $\delta H$ characterizes forces of specific interactions, and applying said composition to said skin, lips of the face, superficial body growths, or any combination thereof, to limit, decrease, or prevent the transfer of said composition from said skin lips of the face, superficial body growths, or any combination thereof.

* * * * *